United States Patent
Dozol et al.

(10) Patent No.: US 6,657,081 B1
(45) Date of Patent: Dec. 2, 2003

(54) CALIXARENE DERIVATIVES

(75) Inventors: Jean-François Dozol, Pierrevert (FR); Alejandro Garcia Carrera, Provence (FR); Volker Bohmer, Mainz (DE); Susan E. Matthews, Bicester (GB)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/831,921

(22) PCT Filed: Nov. 24, 1999

(86) PCT No.: PCT/FR99/02893

§ 371 (c)(1), (2), (4) Date: May 29, 2001

(87) PCT Pub. No.: WO00/31087

PCT Pub. Date: Jun. 2, 2000

(30) Foreign Application Priority Data

Nov. 26, 1998 (FR) .............................. 98 14902

(51) Int. Cl.⁷ .............................. C07F 9/53; C07F 17/00
(52) U.S. Cl. ......................................... 564/15; 423/21.5
(58) Field of Search .............................. 423/9, 10, 21.5; 564/15

(56) References Cited

U.S. PATENT DOCUMENTS

| | | | | |
|---|---|---|---|---|
| 3,243,254 A | * | 3/1966 | Sidall ........................... | 423/9 |
| 5,717,126 A | * | 2/1998 | Paciello et al. ............... | 558/78 |
| 5,866,087 A | * | 2/1999 | Dozol et al. ................... | 423/9 |
| 6,306,355 B1 | | 10/2001 | Delmau et al. | |
| 6,312,653 B1 | | 11/2001 | Delmau et al. | |

FOREIGN PATENT DOCUMENTS

WO    WO 96/23800    8/1996

OTHER PUBLICATIONS

Inorganic Chemistry by Lambert et al 39, pp 2033–2041 2000.*
S. Barboso, et al., Journal of the Chemical Society, Perkin Transaction 2., No. 4, pps. 719–723, "Calix(4)Arenes with CMPO Functions at the Narrow RIM. Synthesis and Extraction Properties," Apr. 1999.

U.S. patent application Ser. No. 09/869,961, filed Jul. 10, 2001, Pending

U.S. patent application Ser. No. 09/831,921, filed May 29, 2001, Pending.

* cited by examiner

Primary Examiner—Jean F. Vollano
(74) Attorney, Agent, or Firm—Oblon, Spivak, McClelland, Maier & Neustadt, P.C.

(57) ABSTRACT

The invention relates to new calixarenes according to the formula:

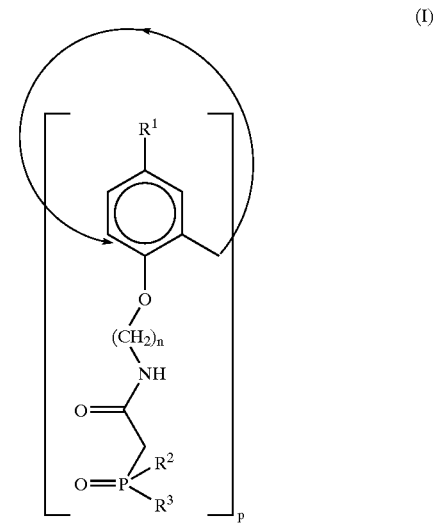

wherein:

$R^1$ is an alkyl or aryl group, or a hydrogen atom, $R^2$ and $R^3$, which may be identical or different, are alkyl or aryl groups, n is an integer ranging from 2 to 8, and p is an integer ranging from 4 to 8.

Said calixarenes may be used to extract actinides and lanthanides from aqueous solutions.

20 Claims, 2 Drawing Sheets

CALIXARENE DERIVATIVES

The application is a 371 of PCT/FR99/02893 filed Nov. 24, 1999, now WO 00/31087.

FIELD OF THE INVENTION

The present invention relates to new calixarene derivatives and the preparation method and use of said derivatives to extract actinides and lanthanides.

More specifically, it relates to calixarenes comprising a phosphinoxide-acetamide substituent, offering beneficial properties for the extraction of actinides and lanthanides, particularly trivalent actinides and lanthanides.

Therefore, said new calixarenes may be used to extract actinides and lanthanides present in aqueous solutions such as aqueous effluents from used nuclear fuel reprocessing installations or used nuclear fuel dissolution solutions.

STATE OF THE RELATED ART

The use of macrocyclic ligands such as calixarenes comprising a phosphinoxide-acetamide substituent, to extract metals such as lanthanides and actinides from aqueous solutions has already been envisaged, as disclosed in WO-A-96/23800 [1].

In said derivatives, the phosphinoxide-acetamide substituent is arranged directly on the phenyl cycles of the calixarene.

DESCRIPTION OF THE INVENTION

The present invention relates to new calixarene derivatives comprising a phosphinoxide-acetamide substituent which is separated from the phenyl groups of the calixarene by a hydrocarbon chain. In addition, said phosphinoxide-acetamide substituent is linked to the hydroxyl function of the calixarene by said hydrocarbon chain.

According to the invention, the calixarene complies with the formula:

(I)

wherein:
- $R^1$ is an alkyl or aryl group, or a hydrogen atom,
- $R^2$ and $R^3$, which may be identical or different, are alkyl or aryl groups,
- n is an integer ranging from 2 to 8, and
- p is an integer ranging from 4 to 8.

In this calixarene, the presence of a hydrocarbon chain between the phosphinoxide-acetamide group and the phenyl cycle is of interest since it makes it possible to adjust the extraction efficiency of the calixarene with respect to actinides and lanthanides.

Indeed, said efficiency increases with the number of carbon atoms in the hydrocarbon chain $(CH_2)_n$, where the number of carbon atoms n may range from 2 to 8, preferentially from 2 to 5.

In formula I given above, $R^1$ may represent a hydrogen atom or an alkyl or aryl group. The alkyl groups liable to be used are linear or ramified alkyl groups, preferentially comprising 1 to 18 carbon atoms.

An example of an $R^1$ group includes the tert-butyl group.

In formula I given above, $R^2$ and R3 may be alkyl or aryl groups. The alkyl groups may be linear or ramified and preferentially have 1 to 18 carbon atoms. The aryl groups that may be used for $R^1$, $R^2$ and $R^3$ are monovalent groups derived from an aromatic or heterocyclic nucleus by removing a hydrogen atom from one of the carbon atoms of the cycle. Examples of such groups include phenyl, naphthyl, pyridyl, thiophenyl and substituted phenyl groups. Preferentially, $R^2$ and $R^3$ represent the phenyl group.

The calixarenes according to the invention may comprise 4 to 8 phenyl cycles. Preferentially, the calixarene comprises 4 phenyl cycles (p=4).

The calixarenes according to formula I according to the invention may be prepared using a method consisting of reacting an amino-alcoxy calixarene derivative according to the formula:

(II)

wherein $R^1$, n and p are as defined above, with a phosphinoxide-acetate according to the formula:

(III)

wherein:
$R^2$ and $R^3$ are as defined above and $R^4$ represents the p-nitrophenyl or 2,4-dinitrophenyl group.

The phosphinoxide acetate according to formula III used in the last step may be prepared using the corresponding alkyl phosphinite according to the formula:

where $R^2$ and $R^3$ have the correspondences given above and $R^5$ is an alkyl group comprising 1 to 4 carbons, by means of a reaction of said group with ethyl bromoacetate, followed by hydrolysis and esterification of the acid obtained with nitrophenol or dinitrophenol.

According to a first embodiment of the invention, the aminoalcoxy calixarene derivative according to formula II wherein n is greater than 2, is prepared using a method comprising the following steps:

1) reaction of a calixarene according to the formula:

(IV)

where $R^1$ and p have the correspondence given above with an N-3(bromoalkyl)phthalimide according to the formula:

(V)

where n has the correspondence given above, to obtain a (3-phthalimido-alcoxy)calixarene according to the formula:

(VI)

and 2) reaction of the compound according to formula VI with hydrazine.

According to a second embodiment of the invention, the aminoalcoxy calixarene derivative according to formula II wherein n=2 is prepared using a method comprising the following steps:

1) reaction of a calixarene according to the formula:

(IV)

wherein:

$R^1$ and p have the correspondence given above, with an alkyl bromoacetate, to obtain the calixarene derivative according to the formula:

(VII)

where $R^1$ has the correspondence given above and $R^5$ represents an alkyl group, 2) reduction of the calixarene derivative according to formula VII to obtain the hydroxylated derivative according to the formula:

(VIII)

3) reaction of the hydroxylated derivative according to formula VIII with tosyl chloride to obtain the tosylated derivative according to the formula:

(IX)

wherein Ts represents the tosyl group, and 4) reaction of the tosylated derivative according to formula IX with $NaN_3$, followed by a catalytic hydrogenation to obtain the calixarene according to formula II where n=2.

The calixarenes according to formula I of the invention may be used to separate at least one metal selected from actinides and lanthanides present in an aqueous solution, such as dissolution solutions and aqueous effluents from used nuclear fuel reprocessing installations, particularly a nitric solution containing 1 to 4 mol/l of $HNO_3$.

To carry out this separation, the aqueous solution containing the metal(s) to be separated is placed in contact with a non-miscible phase comprising at least one calixarene complying with formula I given above, to extract the metal (s) in the non-miscible phase.

Said non-miscible phase is generally composed of a solution of the calixarene(s) according to the invention in a suitable organic solvent.

Examples of solvents that may be used include alkyl benzenes and nitrophenyl alkyl ethers.

Preferentially, an ether such as ortho-nitrophenyl hexyl ether is used as the solvent.

The calixarene concentration of the non-miscible liquid phase particularly depends on the solvent used. Concentrations ranging from $10^{-4}$ to $5.10^{-2}$ mol/l, for example a $10^{-3}$ mol/l concentration, may be used.

To implement the separation method according to the invention, the aqueous solution may be placed in contact with said non-miscible liquid phase in conventional installations such as mixers-clarifiers, centrifugal extractors, pulsating columns, etc., but also by means of supported liquid membranes.

The supported membrane technique consists of immobilising the non-miscible liquid phase on a solid substrate such as polypropylene. Using this technique, it is possible to transfer the metals to be separated from the aqueous solution in which they are contained into an aqueous re-extraction solution. In this case, one of the sides of the membrane is in contact with the first aqueous solution containing the metals to be separated and the other side is in contact with an aqueous re-extraction solution.

The substrate of the supported liquid membrane may be a microporous membrane wherein the pores are filled with calixarene in solution in a suitable organic solvent. Said microporous membrane may be made of polypropylene, polyvinylidene fluoride or polytetrafluorethylene. Said membrane may be used as a separation between a first compartment with the aqueous solution containing the metals to be separated and a second compartment with the aqueous re-extraction solution.

To obtain satisfactory extraction with supported liquid membranes, it is advantageous to use thin, highly porous membranes with a small pore diameter. Said membranes may be used in the form of plane membrane or hollow fibre ultra- or microfiltration modules to process high fluid flow rates.

After the extraction of the metal(s) to be separated in the non-miscible liquid phase, they may be recovered by re-extraction in an aqueous re-extraction solution. Said solution may be an aqueous complexing agent solution. The complexing agent may be an organic acid or an organic acid salt such as methylene diphosphonic acid, oxalic acid, citric acid, oxalates and citrates. The use of such solutions makes it possible to obtain the re-extraction of separated metals with high yields.

The invention's other characteristics and advantages will be seen more clearly on reading the following examples, which are naturally given as an illustration and are not exhaustive, with reference to the appended figures.

DETAILED DESCRIPTION OF EMBODIMENTS

Examples 1 and 2 illustrate the preparation of calixarenes complying with formula I given above, where $R^1$ represents the tert-butyl group, $R^2$ and $R^3$ represent the phenyl group Ph, p is equal to 4 and n is equal to 3 (example 1) and 4 (example 2).

Figure 1:
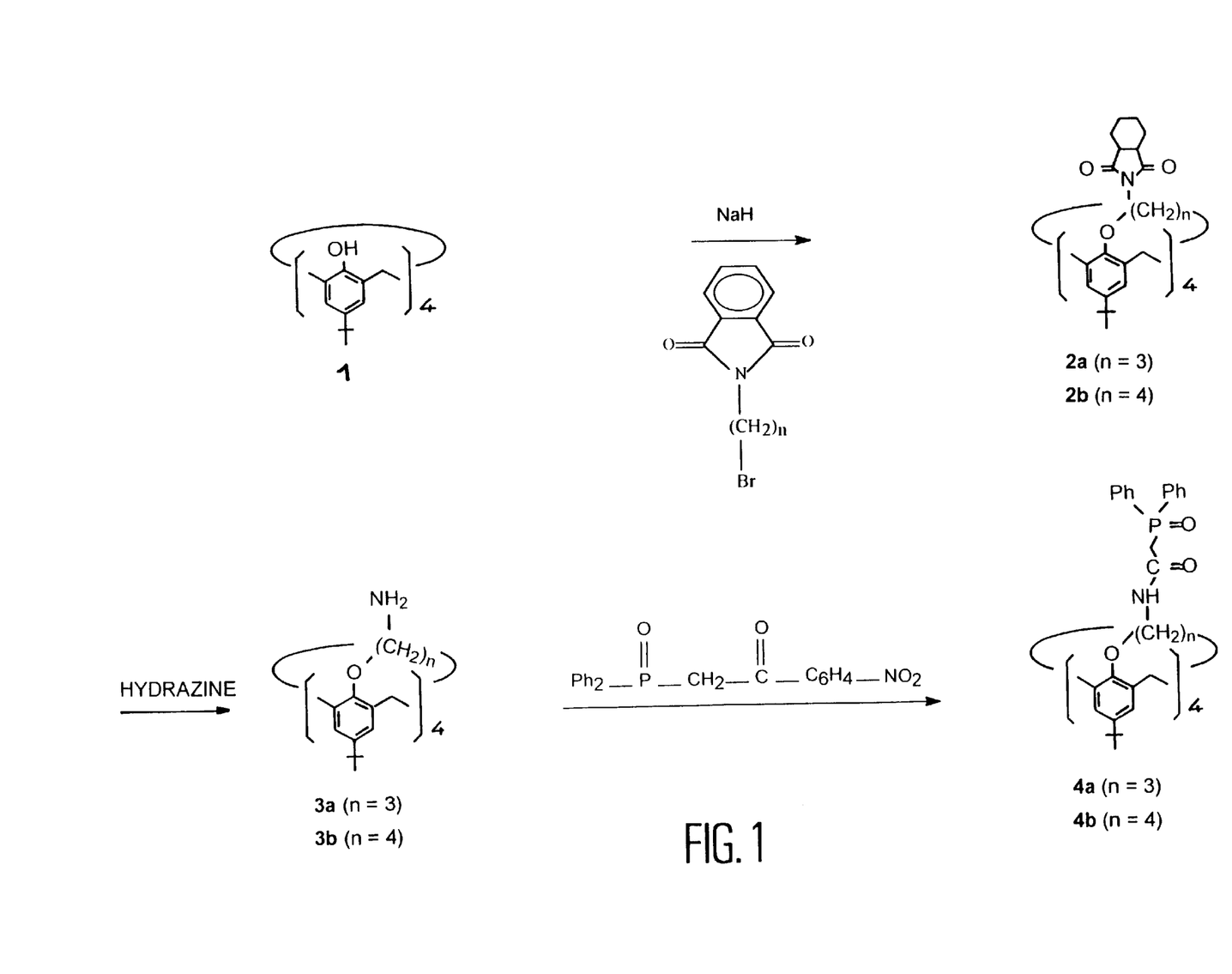
FIG. 1 is a diagram representing the synthesis of calixarenes according to formula I according to the first embodiment of the invention.

In both examples, the synthesis diagram represented in FIG. 1, corresponding to the first embodiment of the method according to the invention, is used.

EXAMPLE 1

Preparation of tetrakis(3-diphenyl-phosphinoxide-acetamide-propoxy)-p-tert-butyl calix[4]arene (compound 4a)

a) Preparation of tetrakis(3-phthalimidopro-poxy)-p-tert-butyl calix[4]arene (Compound 2a)

A suspension of 10 g (15.44 mM) of p-tert-butyl calix[4] arene (compound 1) in 200 ml of dimethylformamide (DMF) is subjected to stirring in argon for 30 minutes. 3.12 g (123.52 mM) of NaH and 320 ml of DMF are then added and stirring is continued for 1 hour. 33.12 g (123.52 mM) of N-3(bromopropyl)phthalimide is then added and stirring of the mixture is continued for 7 days at ambient temperature. 100 ml of water is then added and the resulting precipitate is collected. The precipitate is dissolved in 200 ml of chloroform, washed with 50 ml of 15% HCl and dried on magnesium sulphate ($MgSO_4$). The evaporation of the solvent followed by a precipitation using a chloroform-methanol mixture gives the raw product. By means of silica column chromatography in a chloroform-methanol mixture (4:1), 11.56 g of compound 2a is obtained in the form of a white solid, corresponding to a 54% yield.

The characteristics of the compounds are as follows:

Melting point: 213–215° C.

Rf=0.44 (chloroform:methanol 30:1)

MS (FD) m/z: 1398.8 ($M^+$, calc. 1397.7)

$^1$H NMR (200 MHz, $CDCl_3$ δ: 1.03 (s, 36H, t-Bu), 2.38(quin, 8H, J=7.3 Hz, $CH_2CH_2N$), 3.10 (d, 4H, J=12.7 Hz, $ArCH_2Ar$), 3.86 (t, 8 H, J=7.1 Hz, $CH_2N$), 3.97(t, 8 H, J=7.3 Hz, $OCH_2$), 4.35 (d, 4 H, J=12.7 Hz, $ArCH_2Ar$), 6.71 (s, 8 H, Ar), 7.59 (m, 8 H, Ar-Pht) 7.69 (m, 8 H, Ar-Pht).

b) Preparation of tetrakis(3-aminopro-poxy)-p-tert-butyl calix[4]arene (Compound 3a)

13.29 ml (273 mM) of hydrazine is added to a suspension of 2 g (1.43 mM) of compound 2a in 60 ml of ethanol. The mixture is reflux-heated for 12 hours, cooled and then diluted with 100 ml of water. A precipitate is formed, which is extracted in dichloromethane (4×50 ml). The organic layer is dried on $MgSO_4$ and the solvent is evaporated to obtain 1.22 g of compound 3a (98% yield).

The characteristics of compound 3a are as follows:

Melting point: 197–201° C.

MS(FD): m/z: 878.8 ($M^+$, calc. 877.6)

$^1$H NMR (200 MHz, $CDCl_3$ δ: 1.05 (s, 36H, t-Bu), 2.14(quin, 8H, J=7.32, $CH_2CH_2N$), 2.27 (s large, 8 H, $NH_2$), 2.91 (t, 8 H, J=7.1 Hz, $CH_2NH_2$), 3.11 (d, 4 H, J=12.2 Hz, $ArCH_2Ar$), 3.89(t, 8H, J=7.1 Hz, $OCH_2$), 4.33 (d, 4 H, J=12.2 Hz, $ArCH_2Ar$), 6.75 (s, 8 H, Ar).

c) Preparation of tetrakis(3-diphenylphos-phinoxide-acetamide-propoxy)-p-tert-butyl calix[4]arene (Compound 4a)

2.18 (5.72 mM) of p-nitrophenyl(di-phenylphosphoryl)acetate and 1.0 g (1.14 mM) of compound 3a are heated to 50° C. in 40 ml of toluene, for 18 hours. The solvent is then evaporated and the residue is taken up with chloroform. The solution is washed repeatedly with 5% $Na_2CO_3$, dried on $MgSO_4$, and the solvent is eliminated in a vacuum. Recrystallisation using a chloroform-hexane mixture gives 1.59 g of compound 4a in the form of a white solid (75% yield).

The characteristics of compound 4a are as follows:

Melting point: 244–246° C.

Rf=0.40 (chloroform-methanol 9:1)

MS(FD): m/z: 1848.4 ($M^+$, calc. 1845.8)

$^1$H NMR (200 MHz), $CDCl_3$ δ: 1.04 (s, 36H, t-Bu), 1.99(m large, 8 H, $CH_2CH_2N$), 3.00 (d, 4 H, J=12.2 Hz, $ArCH_2Ar$), 3.27(m large, 8 H, $CH_2N$), 3.48 (d, 8 H, J=14.1 Hz, $POCH_2CO$), 3.65 (t large, 8 H, $OCH_2$), 4.14(d, 4 H, J=12.7 Hz $ArCH_2Ar$), 6.71 (s, 8 H, Ar), 7.31–7.78 (m, 40 H, P—Ar), 8.27 (m large, 4 H NH).

EXAMPLE 2

Preparation of tetrakis(4-diphenyl-phosphinoxide-acetamide butoxy)-p-tert-butyl calix[4]arene (Compound 4b)

a) Preparation of tetrakis(4-(phthalimido-butoxy)-p-tert butyl calix[4]arene (Compound 2b)

A suspension of 2.5 g (3.86 mM) of p-tert butyl calix[4]arene (compound 1) in 50 ml of DMF is subjected to stirring in argon for 30 minutes. 780 mg (30.88 mM) of NaH and 50 ml DMF are added and stirring is continued for 1 hour. 33.12 g (123.52 mM) of N-4(bromobutyl)phthalimide is then added and stirring of the mixture is continued for 5 days at ambient temperature. 50 ml of water is added and the resulting precipitate is collected. The precipitate is dissolved in 200 ml of chloroform, washed with 50 ml of 15% HCl and brine, and dried on $MgSO_4$. The evaporation of the solvent followed by a precipitation using chloroform-methanol gives the raw product. By means of silica column chromatography in chloroform, 2.32 g of compound 2b is obtained in the form of a white solid (42% yield).

The characteristics of compound 2b are as follows:

Melting point: 138–141° C.

Rf=0.45 (chloroform-methanol 30:1)

MS(FD): m/z: 1453.8 ($M^+$, calc. 1453.7)

$^1$H NMR (200 MHz), $CDCl_3$ δ: 1.05 (s, 36 H, t-Bu), 1.75(m large, 8 H, $CH_2CH_2NH_2$), 2.08 (m large, 8 H, $OCH_2CH_2CH_2$), 3.08 (d, 4 H, J=12.7 Hz, $ArCH_2Ar$), 3.75(t, 8 H, J=7.3 Hz, $CH_2N$), 3.90 (t, 8 H, J=7.6 Hz, $OCH_2$), 4.34 (d, 4 H, J=12.2 Hz, $ArCH_2Ar$), 6.73(s, 8 H, Ar), 7.61 (m, 8 H, Ar-Pht), 7.70 (m, 8 H, Ar-Pht).

b) Preparation of tetrakis 4-(amino-butoxy)-p-tert butyl calix[4]arene (Compound 3b)

6.5 ml (133.9 mM) of hydrazine is added to a suspension of 1.0 g (0.68 mM) of compound 2b in 30 ml of ethanol. The mixture is reflux-heated for 12 hours, cooled and then diluted with 100 ml of water. The ethanol is eliminated in a vacuum and the resulting suspension extracted with chloroform (4×100 ml). The organic layer is dried on $MgSO_4$ and the solvent is evaporated to obtain 458 mg of compound 3b in the form of a pale yellow solid (87% yield).

The characteristics of compound 3b are as follows:

Melting point: 195–200° C.

MS(FD): m/z: 934.2 ($M^+$, calc. 933.7)

$^1$H NMR (200 MHz, $CDCl_3$ δ: 1.05 (s, 36 H, t-Bu), 1.58(m large, 8 H, $CH_2CH_2NH_2$), 1.98 (m large, 8 H, $OCH_2CH_2CH_2$), 2.54 (s large, 8 H, $NH_2$), 2.80(t, 8 H, J=7.1 Hz, $CH_2NH_2$), 3.10 (d, 4 H, J=12.7 Hz, $ArCH_2Ar$), 3.85(t, 8 H, J=7.6 Hz, $OCH_2$), 4.34 (d, 4 H, J=12.7 Hz, $ArCH_2Ar$), 6.72 (s, 8 H, Ar).

c) Preparation of Compound 4b 1.03 g (2.7 mM) of p-nitrophenyl(diphenylphosphoryl)acetate and 500 mg (0.54 mM) of compound 3b are heated to 50° C. in 20 ml of toluene, for 18 hours. The solvent is then evaporated and the residue is taken up with chloroform. The solution is washed repeatedly with 5% $Na_2CO_3$, dried on $MgSO_4$, and the solvent is eliminated in a vacuum. Precipitation using chloroform-diethyl ether gives 801 mg of compound 4b in the form of a slightly tinted white solid (78% yield).

The characteristics of compound 4b are as follows:

Melting point: 232–236° C.

Rf=0.29 (chloroform:methanol 9:1)

MS(FD) m/z: 1902.0 ($M^+$, calc. 1901.9)

$^1$H NMR (200 MHz, $CDCl_3$ δ: 1.05 (s, 36 H, t-Bu), 1.41(m large, 8 H, $CH_2CH_2NH_2$), 1.82 (m large, 8 H, $OCH_2CH_2CH_2$), 3.07 (d, 4 H, J=12.7 Hz, $ArCH_2Ar$), 3.15 (br, 8 H, $CH_2NH$), 3.56 (d, 8 H, J=14.2 Hz, $POCH_2CO$), 3.85 (t large, 8 H, $OCH_2$), 4.23 (d, 4 H, J=12.2 Hz, $ArCH_2Ar$), 6.73(s, 8 H, Ar), 7.38–7.84 (m, 40 H, P—Ar), 8.28 (s large, 4 H, NH).

EXAMPLE 3

Preparation of tetrakis(2-diphenyl-phosphinoxide-acetamide-etoxy)-p-tert-butylcalix[4]arene (compound 10)

This compound complies with formula I wherein $R^1$ is the tert-butyl group, p=4, n=2, and $R^3$ and $R^4$ represent the phenyl group.

Figure 2:
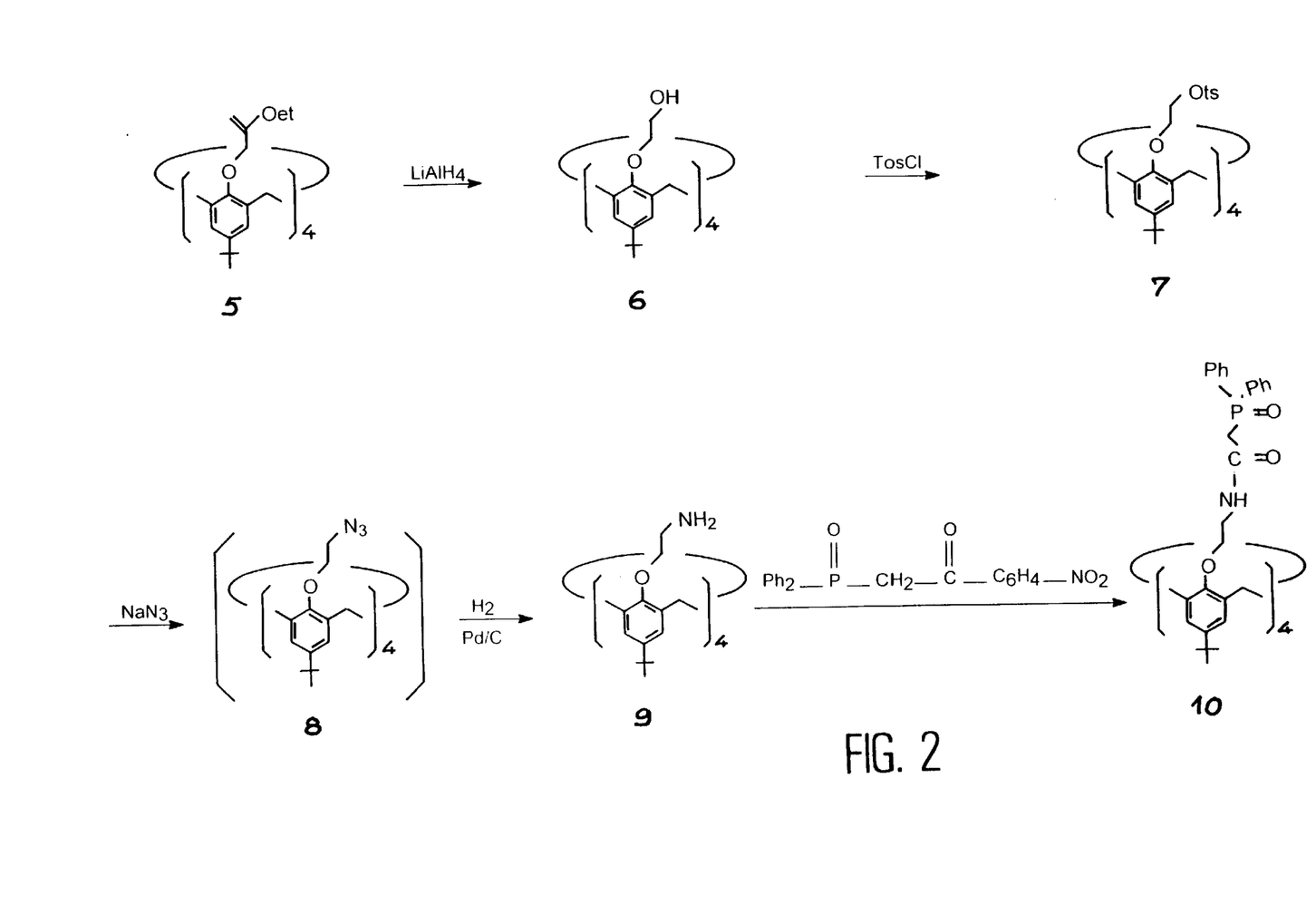
FIG. 2 is a diagram representing the synthesis of calixarenes according to formula I according to the second embodiment of the invention.

For this preparation, the synthesis diagram given in FIG. 2 is followed.

a) Preparation of tetraethyl-p-tert-butyl calix[4]arene tetra-acetate (Compound 5)

8 g (12.35 mM) of p-tert-butyl calix[4]arene (compound 1) and 5 g (36.23 mM) of $K_2CO_3$ are reflux-heated for 1 hour in 250 ml of acetonitrile. 20 ml (180 mM) of ethyl bromoacetate is added and the mixture is reflux-boiled for 48 hours. The solvent is evaporated and the residue is taken up with a mixture of 100 ml water and 100 ml chloroform. The organic layer is separated and washed three times with 50 ml of water. The solution is dried and concentrated in a vacuum. Adding methanol and storing in a refrigerator gives 10.12 g of compound 5 in the form of white crystals (82% yield).

The characteristics of compound 5 are as follows:

Melting point: 128–131° C.

Rf=0.27 (chloroform:methanol 9:1)

MS(FD) m/z: 992.8 ($M^+$, calc. 993.6)

$^1$H NMR (200 MHz, $CDCl_3$ δ: 1.05 (s, 36 H, t-Bu), 1.26(t, 12 H, J=7.1 Hz, $CH_2CH_3$), 3.17 (d, 4 H, J=12.7 Hz $ArCH_2Ar$), 4.18 (quart, 8 H, J=7.3 $CH_2CH_3$), 4.78 (s large, 8 H, $OCH_2$) 4.83(d, 4 H, J=13.2 Hz, $ArCH_2Ar$), 6.75 (s, 8 H, Ar).

b) Preparation of tetrakis(2-hydroxy-ethoxy)-p-tert-butyl calix[4]arene (compound 6)

8 g (8.05 mM) of compound 5 in 50 ml of diethyl ether is added drop by drop to a cooled suspension of 2.44 g (64.38 mM) of $LiAlH_4$ in 50 ml of diethyl ether, in argon. The resulting suspension is left to return to ambient temperature and stirred for 3 days. The suspension is cooled and 1N HCl is added slowly until the solid is dissolved. The aqueous layer is then extracted with a mixture of diethyl ether and dichloromethane (1:1). The organic layer is then washed with water and filtered. The evaporation of the solvent and precipitation using a dichloromethane-methanol mixture gives 5.72 g of compound 6 in the form of a cottony white solid (86% yield).

The characteristics of compound 6 are as follows:

Melting point: 249–296° C.

Rf=0.55 (chloroform:methanol 9:1)

MS(FD) m/z: 824.9 ($M^+$, calc. 825.5)

$^1$H NMR (200 MHz), $CDCl_3$ δ: 1.07 (s, 36 H, t-Bu), 3.20 (d, 4 H, J=12.7 Hz $ArCH_2Ar$), 3.67 (s large, 4 H, OH), 3.98 (s large, 16 H, $CH_2CH_2$), 4.33 (d, 4 H, J=12.7 Hz, $ArCH_2Ar$), 6.83 (s, 8 H, Ar).

c) Preparation of tetrakis[(4-methylphenyl)sulfonyloxyethoxy]-p-tert-butyl calix[4]arene (Compound 7)

13.98 g (73.3 mM) of p-toluenesulfonyl chloride (TosCl) is added to a 5 g (6.07 mM) solution of compound 6, at 0° C. The resulting solution is stored at 4° C. for 4 days, and then poured into 1250 ml of chilled 2N HCl. The oily precipitate is collected and dissolved in dichloromethane. The solution is washed with 2N HCl and brine. Pulverisation with hot hexane followed by chromatography (chloroform-methanol 20:1) gives 5.53 g of compound 7 in the form of a white solid (63% yield).

The characteristics of compound 7 are as follows:

Melting point: 146–149° C.

Rf=0.66 (chloroform:methanol 30:1)

$^1$H NMR (200 MHz), $CDCl_3$ δ: 1.03 (s, 36 H, t-Bu), 2.41 (s, 12 H, $SO_3ArCH_3$) 2.97 (d, 4 H, J=13.2 Hz, $ArCH_2Ar$), 4.07 (s large, 8 H, $ArOCH_2CH_2$), 4.20 (d, 4 H, J=12.7 Hz, $ArCH_2Ar$), 4.37 (s large, 8 H, $ArOCH_2$), 6.67 (s, 8 H, Ar), 7.31 (d, 8 H, J=7.8 Hz, $ArSO_3$), 7.78 (d, 8 H, J=8.3 Hz, $ArSO_3$).

d) Preparation of tetrakis(2-aminoethoxy)-p-tert-butyl calix[4]arene (Compound 9)

405 mg (6.21 mM) of $NaN_3$ is added to a 1.5 g (1.035 mM) solution of compound 7 in 20 ml of DMF. the solution is stirred at 60° C., in argon, for 4 hours. The solution is cooled and diluted with 200 ml of water. The resulting suspension is extracted with 4×75 ml of diethyl ether. The combined organic layers are washed with water, dried on $MgSO_4$ and the solvent is eliminated in a vacuum.

A catalytic quantity of Pd/C is added to the resulting oil (compound 8) in a dioxane-ethanol (1:1) mixture. Gaseous hydrogen is introduced and the mixture is stirred for 48 hours. The mixture is filtered on a celite® base and the solvent is evaporated to obtain the raw amine 9 in the form of a pale green foam. This product is used with no additional purification.

The characteristics of compound 9 are as follows:

MS(FD): m/z: 821.7 ($M^+$, calc. 821.6)

$^1$H NMR (200 MHz), $CDCl_3$ δ: 1.43 (s, 36 H, t-Bu), 1.95 (d, 4 H, J=13.2 Hz, $ArCH_2Ar$), 2.60 (m large, 16 H, $NH_2+CH_2NH_2$), 2.81 (s large, 8 H, $OCH_2$), 3.26 (d, 4 H, J=12.7 Hz, $ArCH_2Ar$), 5.59 (s, 8 H, Ar).

e) Preparation of Compound 10

500 mg (0.61 mM) of raw compound 9 and 1.164 g (3.05 mM) of p-nitrophenyl(diphenylphosphoryl)acetate in 20 ml of toluene containing 2 ml of triethylamine, are heated to 50° C., for 18 hours. The solvents are evaporated and the residue is taken up with chloroform. The organic layer is washed repeatedly with $Na_2CO_3$, dried on $MgSO_4$ and the solvent is eliminated in a vacuum. The raw product undergoes chromatography on a silica column in chloroform-methanol (20:1), which gives 700 mg of compound 9 in the form of a pale brown vitreous compound (43% yield using compound 7).

The characteristics of compound 10 are as follows:

Rf=0.32 (chloroform: methanol 9:1)

$^1$H NMR (200 MHz), $CDCl_3$+DMSO-$d_6$ δ: 0.90 (s large, 36 H, t-Bu), 2.82 (d, 4 H, J=12.7 Hz, $ArCH_2Ar$), 3.30 (d, 8 H, J=13.2 Hz, $POCH_2CO$), 3.49 (m large, 8 H, $NHCH_2$), 3.69 (m large, 8H, $OCH_2$), 3.92 (d, 4 H, J=12.7 Hz, $ArCH_2Ar$), 6.54 (s large, 8 H, Ar), 7.12–7.64 (m, 40 H, P—Ar), 8.27 (s large, 4 H, NH).

EXAMPLE 4

In this example, the efficiency of the calixarene in example 3 (compound 10) to separate lanthanum, cerium, neodymium, samarium, europium, americium and curium is evaluated, using aqueous solutions containing one of these elements, the nitric acid in the solutions varying from $10^{-2}$ mol/l to 4 mol/l.

In this example, 3 ml of each solution containing approximately $10^{-5}$ mol/l of the element to be separated is placed in contact with 3 ml of an organic solution composed of nitrophenylhexyl ether (NPHE) containing $10^{-3}$ mol/l of compound 10. The substances are placed into contact in a 20 ml polypropylene tube subjected to stirring. After 1 hour of contact, the two phases are allowed to settle and the activity of each phase is counted by liquid scintillation or by α or γ spectrophotometry.

The distribution coefficient D, which corresponds to the ratio of the activity of the element in the organic phase over the activity of said element in the aqueous phase, is then determined.

The results obtained are given in table 1.

These results show that the distribution coefficients increase with the acidity of the aqueous solution.

EXAMPLE 5

In this example, the same procedure as in example 4 is followed to test the efficiency of compound 4a for the separation of the same elements. The results obtained are given in table 2 attached.

As for compound 10, the distribution coefficients increase with the acidity of the initial aqueous solution. In addition, the distribution coefficients are higher than for compound 10 which comprises a shorter hydrocarbon chain between the phosphinoxide-acetamide group and the phenyl cycle of the calixarene.

EXAMPLE 6

In this example, the same procedure as in example 4 is followed to test the efficiency of compound 4b for the separation of the same elements using nitric solutions. The results obtained are given in table 3.

These results demonstrate that the distribution coefficients still increase with the acidity of the aqueous solution, but they are much higher when the hydrocarbon chain comprises 4 carbon atoms.

It is particularly important to note that the calixarenes 4a and 4b have high distribution coefficients for Am and Cm.

Comparative Example

In this example, the same procedure as in example 4 is followed, but CMPO at a concentration of 0.25 mol/l in nitrophenyl hexyl ether is used as the liquid phase to separate the same. The formula of CMPO is as follows:

(iBu = isobutyl)

The results obtained are given in table 4.

If the results in table 4 are compared to those in table 3 for calixarene 4b, it is noted that the use of CMPO requires much higher concentrations (0.25 mol/l instead of $10^{-3}$ mol/l) to obtain results of the same order of magnitude.

Therefore, the calixarenes according to the invention are much more beneficial.

REFERENCE

[1]: WO-A-96/23800.

TABLE 1

DISTRIBUTION COEFFICIENTS
Compound 10/($10^{-3}$M) in NPHE

| $HNO_3$ | $10^{-2}$M | $10^{-1}$M | 1M | 1.5M | 2M | 3M | 4M |
|---|---|---|---|---|---|---|---|
| La | 0.18 | 0.27 | 1.85 | 2.40 | 2.60 | 3.10 | 4.00 |
| Ce | 0.28 | 0.31 | 2.00 | 2.65 | 2.90 | 3.65 | 5.05 |
| Nd | 0.28 | 0.17 | 1.25 | 1.65 | 1.90 | 2.70 | 3.95 |
| Sm | 0.39 | 0.14 | 1.00 | 1.30 | 1.55 | 2.10 | 3.50 |
| Eu | 0.29 | 0.07 | 0.72 | 1.00 | 1.15 | 1.70 | 2.95 |
| Am | 0.60 | 0.30 | 1.80 | 2.15 | 2.65 | 3.75 | 5.65 |
| Cm | 2.5 | 0.50 | 1.85 | 2.10 | 2.35 | 3.00 | 4.50 |

TABLE 2

DISTRIBUTION COEFFICIENTS
Compound 4a ($10^{-3}$M) in NPHE

| $HNO_3$ | $10^{-2}$M | $10^{-1}$M | 1M | 1.5M | 2M | 3M | 4M |
|---|---|---|---|---|---|---|---|
| La | 0.08 | 0.41 | 2.90 | 2.95 | 2.85 | 2.95 | 3.10 |
| Ce | 0.10 | 0.57 | 3.95 | 4.20 | 4.20 | 4.50 | 4.70 |
| Nd | 0.09 | 0.49 | 3.25 | 3.60 | 3.70 | 4.30 | 4.70 |
| Sm | 0.11 | 0.50 | 3.35 | 3.75 | 4.15 | 5.00 | 5.95 |
| Eu | 0.10 | 0.39 | 2.80 | 3.20 | 3.55 | 4.45 | 5.50 |
| Am | 0.09 | 0.72 | 4.55 | 4.40 | 4.90 | 5.85 | 6.85 |
| Cm | 0.50 | 1.25 | 4.80 | 4.80 | 5.90 | 6.95 | 8.50 |

TABLE 3

DISTRIBUTION COEFFICIENTS
Compound 4b ($10^{-3}$ M) in NPHE

| $HNO_3$ | $10^{-1}$ M | 1 M | 1.5 M | 2 M | 3 M | 4 M |
|---|---|---|---|---|---|---|
| La | 1.57 | 35.7 | 35.6 | 34.9 | 29.9 | 34.6 |
| Ce | 1.95 | 16.4 | 15.3 | 14.9 | 13.9 | 15.4 |
| Nd | 1.62 | 34.8 | 36.4 | 37.0 | 37.5 | 45.6 |
| Sm | 1.63 | 35.9 | 37.5 | 39.9 | 52.5 | 55.7 |
| Eu | 1.28 | 29.02 | 31.2 | 33.6 | 46.6 | 51.9 |
| Am | 2.35 | 47.9 | 47.4 | 51.0 | 61.2 | 63.9 |
| Cm | 8.8 | 43.5 | 51.0 | 34.0 | 43.5 | 53.7 |

TABLE 4

DISTRIBUTION COEFFICIENTS
CMPO (0.25M) in NPHE

| $HNO_3$ | $10^{-2}$M | $10^{-1}$M | 1M | 1.5M | 2M | 3M | 4M |
|---|---|---|---|---|---|---|---|
| La | 0.92 | 12.9 | 67 | 62 | 70 | 51 | 38 |
| Ce | 1.6 | 21 | 14 | 12.5 | 13 | 12.5 | 11.5 |
| Nd | 1.7 | 23 | 125 | 115 | 135 | 100 | 75 |
| Sm | 1.6 | 21 | 140 | 130 | 160 | 110 | 90 |
| Eu | 1.2 | 16 | 110 | 105 | 125 | 90 | 75 |
| Am | 2.5 | 35 | 200 | 155 | 195 | 150 | 105 |
| Cm | 1.7 | 26 | 90 | 95 | 52 | 50 | 68 |

What is claimed is:

1. Calixarene according to the formula (I):

(I)

wherein:

$R^1$ is an alkyl or aryl group, or a hydrogen atom, $R^2$ and $R^3$, which may be identical or different, are alkyl or aryl groups, n is an integer ranging from 2 to 8, and p is an integer ranging from 4 to 8.

2. Calixarene according to claim 1, wherein p is equal to 4.

3. Calixarene according to claim 1, wherein $R^1$ represents a tert-butyl group.

4. Calixarene according to claim 1, wherein $R^2$ and $R^3$ represent a phenyl group.

5. Calixarene according to claim 1, wherein n is an integer from 2 to 5.

6. Calixarene according to claim 1, wherein:

$R^1$ represents the tert-butyl group, $R^2$ and $R^3$ represent the phenyl group, n is equal to 2, 3 or 4, and p is equal to 4.

7. Method to prepare a calixarene according to the formula (I):

(I)

wherein:

$R^1$ is an alkyl or aryl group, or a hydrogen atom, $R^2$ and $R^3$, which may be identical or different, are alkyl or aryl groups, n is an integer ranging from 2 to 8, and p is a number ranging from 4 to 8, which consists of:

reacting an aminoalkoxy calixarene according to the formula (II):

(II)

wherein $R^1$, n and p are as defined above, with a phosphinoxide-acetate according to the formula (III):

(III)

wherein:

$R^2$ and $R^3$ are as defined above and $R^4$ represents a p-nitrophenyl or a 2,4-dinitrophenyl group.

8. Method according to claim 7, wherein the aminoalkoxy calixarene according to formula (II) wherein n is greater than 2, is prepared using a method comprising:

1) reacting a calixarene according to the formula (IV):

(IV)

wherein $R^1$ is an alkyl or aryl group, or a hydrogen atom, and p is a number ranging from 4 to 8; with an N-3 (bromoalkyl)phthalimide according to the formula (V):

wherein n is an integer ranging from 2 to 8, to obtain a (3-phthalimido-alkoxy)calixarene according to the formula (VI):

and

2) reacting the compound according to formula (VI) with hydrazine.

9. Method according to claim 7, wherein the aminoalkoxy calixarene according to formula (II) wherein n=2 is prepared using a method comprising:

1) reacting a calixarene according to the formula (IV):

wherein:
R$^1$ is an alkyl or aryl group, or a hydrogen atom, and
p is a number ranging from 4 to 8; with an alkyl bromoacetate, to obtain the calixarene according to the formula (VII):

wherein R$^1$ is an alkyl or aryl group, or a hydrogen atom, and R$^5$ represents an alkyl group, 2) reducing the calixarene according to formula (VII) to obtain the calixarene according to the formula (VIII):

3) reacting the calixarene according to formula (VIII) with tosyl chloride to obtain the calixarene according to the formula (IX):

wherein Ts represents the tosyl group, and 4) reacting the calixarene according to formula (IX) with NaN₃, followed by a catalytic hydrogenation to obtain the calixarene according to formula (II) where n=2.

10. Method to separate at least one metal which is selected from the group consisting of actinides and lanthanides that are present in an aqueous solution, comprising:

placing the aqueous solution in contact with a non-miscible phase comprising at least one calixarene according to the formula (I):

(I)

wherein
$R^1$ is an alkyl or aryl group, or a hydrogen atom,
$R^2$ and $R^3$, which may be identical or different, are alkyl or aryl groups,
n is an integer ranging from 2 to 8, and
p is an integer ranging from 4 to 8.

11. Method according to claim 10, wherein the aqueous solution is a nitric solution comprising 1 to 4 mol/l of $HNO_3$.

12. Method according to claim 10, wherein the non-miscible phase is a solution of the calixarene according to formula (I) in an organic solvent.

13. Method according to claim 12, wherein the organic solvent is a nitrophenyl alkyl ether.

14. Calixarene according to claim 2, wherein $R^1$ represents a tert-butyl group.

15. Method according to claim 11, wherein the non-miscible phase is a solution of the calixarene according to formula (I) in an organic solvent.

16. Method according to claim 12, wherein the organic solvent is an alkyl benzene.

17. Method according to claim 11, wherein the calixarene according to formula (I) is present in the non-miscible phase ranging from 0.0001 to 0.05 mol/l.

18. Method according to claim 11, wherein the aqueous solution contacts the non-miscible phase in an apparatus selected from the group consisting of mixers-clarifiers, centrifugal extractors and pulsating columns.

19. Method according to claim 11, wherein the aqueous solution contacts the non-miscible phase; wherein the non-miscible phase is immobilized on a solid substrate.

20. Method according to claim 19, wherein the solid substrate is polypropylene.

* * * * *